US008390286B2

(12) United States Patent
Matlashov et al.

(10) Patent No.: US 8,390,286 B2
(45) Date of Patent: Mar. 5, 2013

(54) ULTRA-LOW FIELD NUCLEAR MAGNETIC RESONANCE AND MAGNETIC RESONANCE IMAGING TO DISCRIMINATE AND IDENTIFY MATERIALS

(75) Inventors: Andrei Nikolaevich Matlashov, Los Alamos, NM (US); Algis V. Urbaitis, Albuquerque, NM (US); Igor Mykhaylovich Savukov, Los Alamos, NM (US); Michelle A. Espy, Los Alamos, NM (US); Petr Lvovich Volegov, Los Alamos, NM (US); Robert Henry Kraus, Jr., Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 549 days.

(21) Appl. No.: 12/720,432

(22) Filed: Mar. 9, 2010

(65) Prior Publication Data

US 2010/0219827 A1   Sep. 2, 2010

Related U.S. Application Data

(63) Continuation-in-part of application No. 11/804,799, filed on May 18, 2007, now Pat. No. 7,688,069.

(51) Int. Cl.
*G01V 3/00* (2006.01)
(52) U.S. Cl. .......................... 324/309; 324/318
(58) Field of Classification Search ........... 324/300–322
See application file for complete search history.

(56) References Cited

U.S. PATENT DOCUMENTS 7,688,069 B2 * 3/2010 Kraus et al. .................. 324/309

* cited by examiner

*Primary Examiner* — Tung S Lau
(74) *Attorney, Agent, or Firm* — Juliet A. Jones

(57) ABSTRACT

Method comprising obtaining an NMR measurement from a sample wherein an ultra-low field NMR system probes the sample and produces the NMR measurement and wherein a sampling temperature, prepolarizing field, and measurement field are known; detecting the NMR measurement by means of inductive coils; analyzing the NMR measurement to obtain at least one measurement feature wherein the measurement feature comprises T1, T2, T1ρ, or the frequency dependence thereof; and, searching for the at least one measurement feature within a database comprising NMR reference data for at least one material to determine if the sample comprises a material of interest.

20 Claims, 4 Drawing Sheets

ULTRA-LOW FIELD NUCLEAR MAGNETIC RESONANCE AND MAGNETIC RESONANCE IMAGING TO DISCRIMINATE AND IDENTIFY MATERIALS

CROSS REFERENCE TO RELATED APPLICATION

This application is a continuation-in-part of U.S. patent application Ser. No. 11/804,799, filed May 18, 2007, and incorporated herein by reference in its entirety.

STATEMENT OF FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

FIELD OF THE INVENTION

The present invention relates to an apparatus and method for rapid identification of liquid materials, for example, as part of security measures, using an ultra-low field magnetic resonance imaging (ULF-MRI) system utilizing inductive coil magnetometers as sensors.

BACKGROUND OF THE INVENTION

Recent emphasis on security has placed higher demands on development of detection of threats, including liquid explosives. Any means for detection for public use must be non-invasive, rapid, and be able to distinguish potential threats from, e.g., beverages or common personal care products. Nuclear magnetic resonance (NMR) techniques have long been used to investigate properties of materials ranging from chemical samples to the human body, referred to as magnetic resonance imaging, or MRI. NMR instruments typically employ large superconducting magnets that produce high magnetic fields.

Ultra-low field magnetic resonance imaging in combination with SQUID (superconducting quantum interference device) detectors has been shown to be capable of non-invasively identifying certain hazardous materials in luggage and shipping containers (see U.S. patent application Ser. No. 11/804,799, filed May 18, 2007). Some advantages of ULF-MRI systems include the lack of requirement of large, powerful magnets, and the ability to analyze materials enclosed in conductive and lead shells. SQUID detectors, while remarkably sensitive, require cryogenic cooling. This results in added expense and size, which significantly limits practical applicability.

A need exists, therefore, for a system for threat detection and discrimination of liquids, in particular of liquid explosives or components thereof, which is sensitive, rapid, non-invasive, and which is also relatively inexpensive and portable.

SUMMARY OF THE INVENTION

The present invention meets the aforementioned need by providing an apparatus and method of identification of liquid materials which utilizes ULF-MRI in combination with inductive coil magnetic detectors, which are optimized to operate with ULF-MRI at about a 1 kHz to about 40 kHz Larmor frequency range. The apparatus of the present invention operates at room temperature, and has a signal-to-noise ratio which is sufficient for identification of liquids and distinguishing between common compositions and potential threats. The system does not require cryogenic cooling (e.g., liquid helium).

Inductive coil magnetic detectors have long been used for magnetic measurements. For example, devices for geophysical locating utilize magnetometers which are optimized for detection in the range of about 1 mHz to 1 kHz range. Other applications utilize magnetometers for detection above 50 kHz. However, for the purposes of the present application, detection in the range of about 1 kHz-40 kHz would be required, and prior to this work, it was not thought that inductive coils could be configured to produce a signal with a sufficient resolution so as to replace the use of SQUID detectors. See, e.g., Myers et al., J. Magn. Resonance, 186 (2007) 182-192. Furthermore, although inductive coils have long been used and are well understood, optimization of inductive coils for specific applications is not intuitive even to those well-skilled in the art (see, e.g., Tumanski, "Induction coil sensors—a review," Meas. Sci. Technol. 18 (2007) R31-R46, incorporated herein by reference). Applicants have unexpectedly found, however, that when an optimal coil diameter is used in combination with a sufficiently low-noise electronic amplifier, inductive coils can produce a signal-to-noise ratio which is sufficient to both identify materials and to distinguish between common, harmless compositions and potential threats.

The following describe some non-limiting embodiments of the present invention.

According to one embodiment of the present invention, a method is provided comprising obtaining an NMR measurement from a sample wherein an ultra-low field NMR system probes the sample and produces the NMR measurement and wherein a sampling temperature, prepolarizing field, and measurement field are known; detecting the NMR measurement by means of inductive coils; analyzing the NMR measurement to obtain at least one measurement feature wherein the measurement feature comprises T1, T2 T1ρ and/or the frequency dependence thereof; and, searching for the at least one measurement feature within a database comprising NMR reference data for at least one material, to determine if the sample comprises a material of interest.

According to another embodiment of the present invention, a method is provided comprising measuring a sampling temperature; obtaining an NMR measurement and an interior image from a sample wherein a an ultra-low field NMR system probes the sample and produces the NMR measurement and wherein a sampling temperature, prepolarizing field, and measurement field are known; detecting the NMR measurement by means of inductive coils; analyzing the NMR measurement to obtain at least one measurement feature; searching for the at least one measurement feature within a reference library comprising at least one NMR reference data for at least one material, to determine if the sample comprises a material of interest.

According to yet another embodiment of the present invention, a method is provided comprising passing an container through a scanning system comprising an ultra-low field NMR system wherein the container is unopened, wherein the ultra-low field NMR system probes the container and produces an NMR measurement and wherein a sampling temperature, prepolarizing field, and measurement field are known and wherein the pre-polarizing magnetic field and the measurement magnetic field are different; detecting the NMR measurement by means of inductive coils; analyzing the NMR measurement to obtain at least one measurement feature; searching for the at least one measurement feature within a database comprising NMR reference data for at least one material to determine if the sample comprises a material of interest.

BRIEF DESCRIPTION OF THE DRAWINGS

In the accompanying figures, like reference numerals refer to identical or functionally similar elements throughout the separate views, which are incorporated in and form a part of the specification.

DETAILED DESCRIPTION OF THE INVENTION

Figure 1:
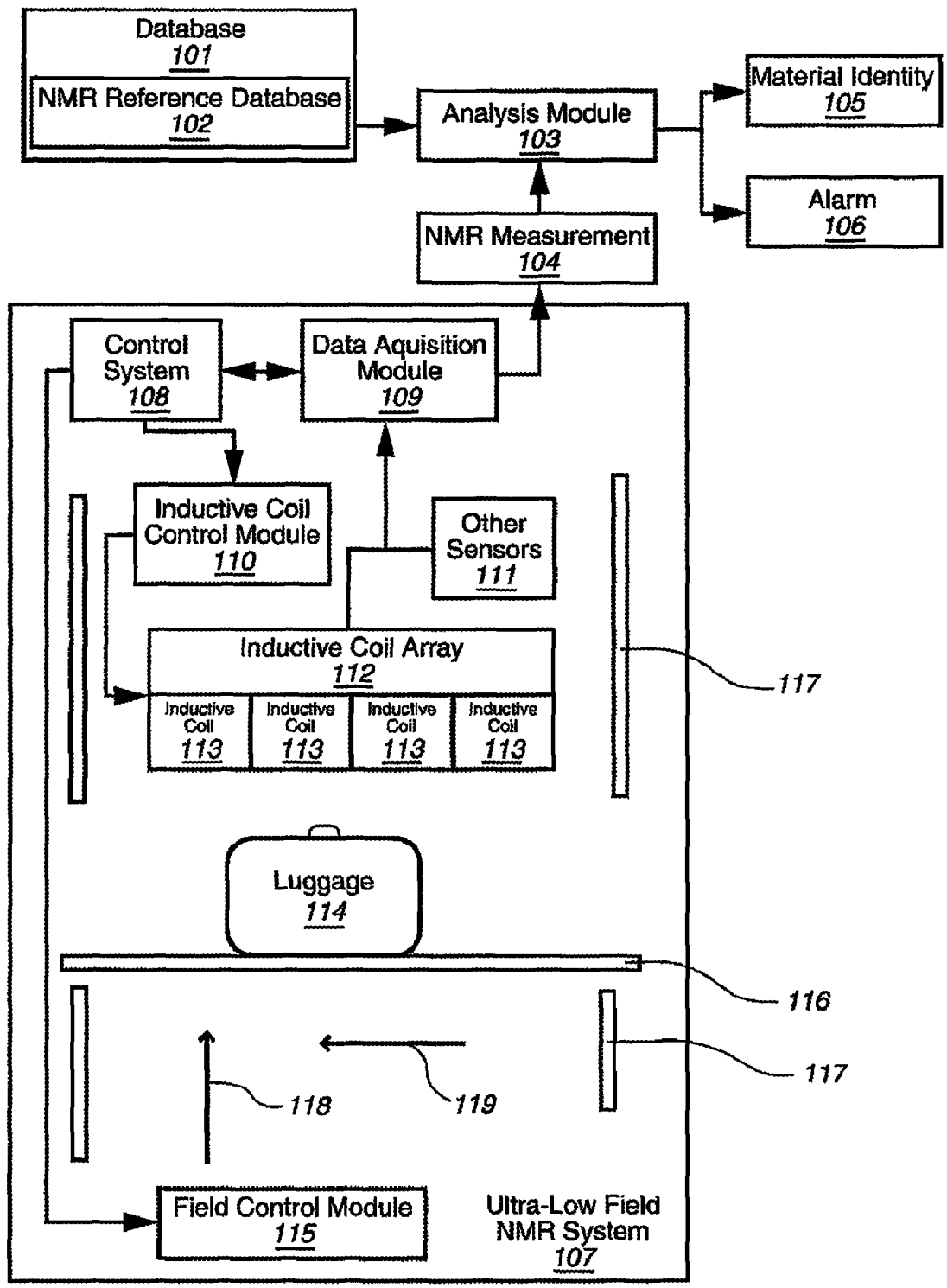
FIG. 1 illustrates a system for examining luggage for materials of interest in accordance with aspects of the embodiments.

It is one aspect of the embodiments to obtain an NMR measurement by probing a sample with an ultra-low field NMR system. An ultra-low field NMR system has separate prepolarizing and measurement fields. Prepolarizing techniques are used to enhance signal-to-noise. The measurement field is typically less than 1 mT (where T is Tesla) which corresponds to a proton Larmor frequency of from about 1 kHz to about 40 kHz.

It is further an aspect of the embodiments that certain measurement parameters are known. Those measurement parameters include those specifying the sampling temperature, the prepolarizing field, and the measurement field.

It is further an aspect of the embodiments to detect the NMR measurement by means of inductive coils.

It is further an aspect of the embodiments to analyze the NMR measurement to obtain one or more measurement features. T1, T2, T1ρ, and the frequency dependence thereof, are examples of measurement features that are well known to those practiced in the art the NMR instrumentation.

It is yet a further aspect of the embodiments to compare the measurement features within a database. The database contains the NMR measurement features of materials of interest, non-limiting examples of which include liquids such as a hazardous material, a food, a beverage, a substance indicative of food quality (such as a by-product of degradation, a marker for a microorganism, etc.), a pharmaceutical product, or a pharmaceutical by-product. For example, a known hydrogen peroxide solution, being a possible explosive precursor, can be examined by a low field NMR system to produce NMR reference data for inclusion in the database. If the measurement features obtained from the NMR measurement are similar to the hydrogen peroxide reference data, then the sample likely contains hydrogen peroxide.

The database can be searched by comparing the data for each NMR reference material to the measurement features of the sample. The measurement features can be expressed as a measurement vector. Similarly, each NMR hazardous material reference can be expressed as a reference vector. Correlations, correlation coefficients, and other distance measures or functions can be used for the comparisons. Thresholds can be used to determine if a comparison has identified a material.

Those practiced in the arts of classification or pattern recognition are familiar with correlations, distances, vectors, thresholds, and techniques for searching for a matching reference within a database.

An ultra-low field NMR system can non-invasively examine closed and/or opaque containers. Database matching techniques can then identify one or more materials of interest within the container. Ultra-low field NMR systems are ideal for this purpose because they do not require large powerful magnets and because they can examine materials enclosed in conductive shells and lead shells. The NMR examination technique can be combined with ultra-low field NMR imaging where an NMR image is obtained and analyzed to identify target volumes. Spatial sensitivity encoding techniques can then be used to identify their contents.

The present invention is useful for identifying and discriminating between materials in various containers. Herein, "container" is understood to mean a non-ferromagnetic container, such as a suitcase (luggage), packaging (such as bottles), and other types of product containers. "Container" is not understood to include large shipping containers, such as are used for shipping of freight. The container may be inside of, or comprise part of, a mammalian body, including a human body. Nonlimiting examples of materials of interest include a liquid hazardous material, a food, a beverage, a substance indicative of food quality, a pharmaceutical product, or a pharmaceutical by-product.

FIG. 1 illustrates a system for examining luggage 114 for materials of interest in accordance with aspects of the embodiments. Luggage 114 can be conveyed on a carrier 116 through an ultra-low field NMR system 107. A control system 108 controls various aspects and modules of the ultra-low field NMR system 107. A field control module 115 controls the prepolarizing field 118 and the measurement field, including imaging gradients 119. The inductive coil control 110 module, comprising inductive coils and their corresponding amplifiers, controls an inductive coil array 112 containing inductive coils 113. The inductive coils of the present invention are inductive coil magnetometers, which are air coils ("donut-shaped") as opposed to search coils (see, e.g., Tumanski, "Induction coil sensors—a review," Meas. Sci. Technol. 18 (2007) R31-R46). The inductive coils of the present invention comprise a conductive wire, such as copper, gold, silver, etc. The inductive coils have an outer diameter (OD) of from about 30 mm to about 300 mm, and in one embodiment have an outer diameter of about 90 mm. The inner diameter (encompassing a hollow space, or "donut hole") may be from about 10 mm to about 50 mm. The inductive coils may have a height of from about 5 mm to about 30 mm, and in one embodiment of about 18 mm. The inductive coils may have an inductance of from about 1 milliHenry (mH) to about 100 mH, and in one embodiment of about 50 mH, and alternatively of about 3 mH. Each individual inductive coil is connected to an amplifier having a gain of at least 1,000 and alternatively of about 10,000, one commercially available example of which is instrumentation amplifier Model INA217, available from Burr-Brown, Tucson, Ariz. A data acquisition module 109 obtains the inductive coil measurements as well as measurements from other sensors 111. The inductive coils may be in resonance or in non-resonance mode. The other sensors 111 can measure the sampling temperature of the container as well as the strengths and polarities of the magnetic fields.

The data acquisition module 109 can pass an NMR measurement module 104 to an analysis module 103 that produces measurement features. The analysis module 103 obtains NMR reference data for at least one material 102 from an NMR reference database 101 for comparison to the measurement features. If the comparison indicates that a material of interest is present, then an alarm 106 can alert people to the presence of a hazardous material. The material identity 105 is the material corresponding to the NMR reference materials 102 that matched the measurement features.

As is well known to those practiced in the art of ultra-low field NMR instrumentation with pulsing prepolarization field, the sensors must often be deactivated while the magnetic prepolarization field 118 is applied. As such, the control system 108 can cause the inductive coils 113 to deactivate before the prepolarization field is 118 is turned on. The inductive coils 113 can be reactivated after the prepolarization field 118 is turned off with the measurement field 119 remaining. Magnetic shielding 117 can adjust the ambient field or isolate the ultra-low field NMR system 107 from sources of interference.

A measurement feature can be dependent or independent of the Larmor frequency. The dependence of measurement features on Larmor frequency can be used for further identification of the material. Additionally, a dependent measurement feature can be made to be independent of the Larmor frequency by mathematically removing or normalizing its effect. Those practiced in the arts of NMR or MRI are familiar with compensating measurement features for their dependence on the Larmor frequency.

In one embodiment, the dependence of measurement features are obtained as a function of the pre-polarizing field strength. The pre-polarizing field strength may be in the range of from about 20 mT (milliTesla) to about 200 mT.

Figure 2:
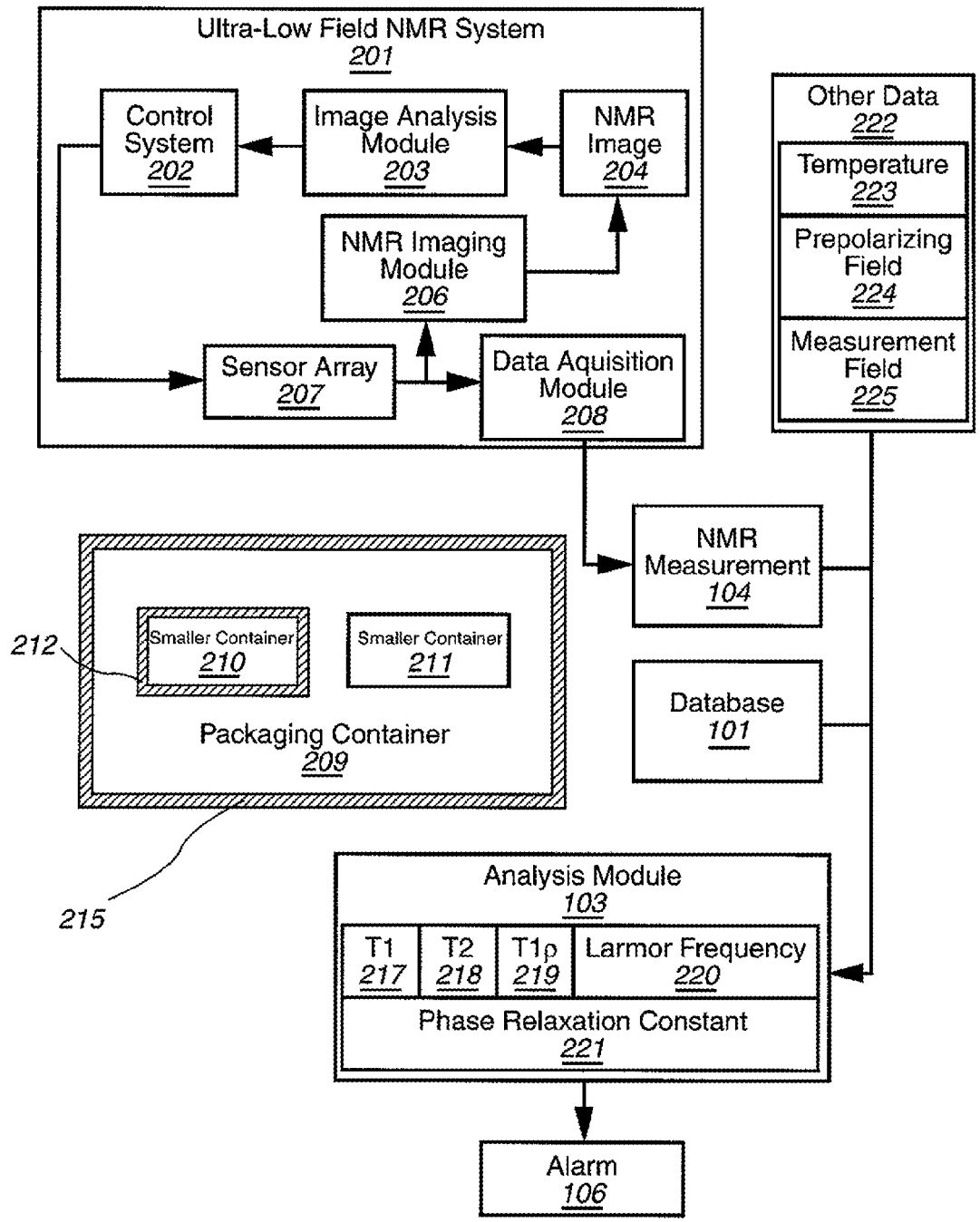
FIG. 2 illustrates a system for imaging container contents while to identify materials of interest, in accordance with aspects of the embodiments.

FIG. 2 illustrates a system for imaging container contents while examining the container for materials of interest in accordance with aspects of the embodiments. A container 209 can contain smaller containers 210, 211. For example, luggage can contain a tube of tooth paste. The container 209 can have a conductive shell 215, for example lead or aluminum. A smaller container 210 can also have a conductive shell 212.

An ultra-low field NMR system 201 can examine the shipping container 208 by first imaging its contents. Imaging can be achieved by spatially varying the prepolarizing or measurement fields. For clarity, the magnetic fields and field control elements are not presented in FIG. 2. One can also use the spatial distribution of sensitivity of each magnetic field sensor channel to distinguish the contents. The control system 202 controls the sensor array 207. The sensor array 207 contains the inductive coils of FIG. 1. Those practiced in the arts of NMR or MRI are familiar with using spatial sensitivity coding and with using the spatial dependence of the prepolarizing and measurement fields to produce images.

The NMR imaging module 206 constructs an NMR image 204 from the output of the sensor array 207. An image analysis module 203 can examine the NMR image 204 to identify target volumes inside the packaging container 209. As illustrated in FIG. 2, the image analysis module has identified a smaller container 210 potentially comprising a material of interest. A target volume containing the smaller container 210 is identified.

The NMR image 204 is an interior image of the packaging container 209. Other imaging devices, such as an X-ray scanner, can also produce interior images. Regardless of the source, an interior image is analyzed to identify target volumes. The other imaging device can be inside or outside of the low field NMR system 201. Most importantly, however, the ultra-low field NMR system 201 can simultaneously act as both an imaging device and as a component of a detection system for a material of interest by NMR measurement of material properties as described for FIG. 1.

The data acquisition module 208 produces an NMR measurement from the sensor array output. The analysis module 103 obtains the NMR measurement 104 as well as other data 222 that can include sampling temperature 223, prepolarizing field parameters 224, and measurement field parameters 225. Magnetic field parameters can include polarity and strength. The analysis module can produce measurement features such as T1 217, T2 218, T1ρ, and/or the frequency-dependence thereof 219, a phase relaxation constant 221, and Larmor frequency 220. The Larmor frequency 220 may be from about 1 kHz to about 40 kHz, and in one embodiment is about 3.2 kHz. A lower frequency is able to penetrate metallic containers. Comparing the measurement features to the contents of a database 101 can result in an alarm 106. The system of the present invention has a signal-to-noise ratio of at least 40 in non-resonance mode and of at least 20 in resonance mode, as compared to conditions under which a sensor system comprising SQUIDs would exhibit a signal-to-noise ratio of about 100.

Figure 3:
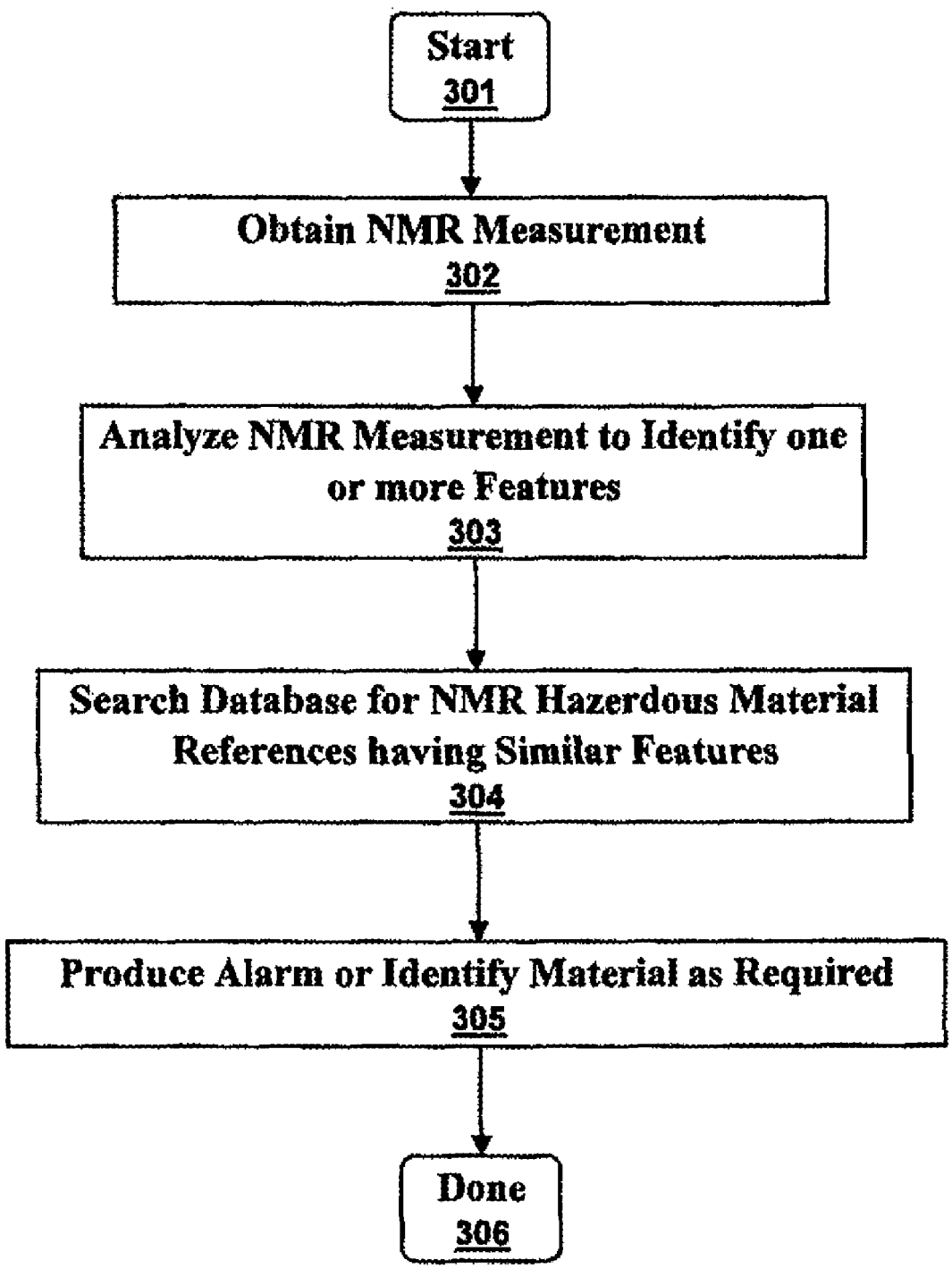
FIG. 3 illustrates a high level flow diagram of a method for identifying materials of interest in accordance with aspects of some embodiments.

FIG. 3 illustrates a high level flow diagram for identifying materials of interest in accordance with aspects of some embodiments. After the start 301, an NMR measurement is obtained 302 and analyzed to identify NMR measurement features 303. Next, a database is searched for NMR reference data for at least one material that are similar to the NMR measurement features 305. If material of interest is indicated, an alarm can be activated and the material can be identified 305 before the process is complete 306.

Figure 4:
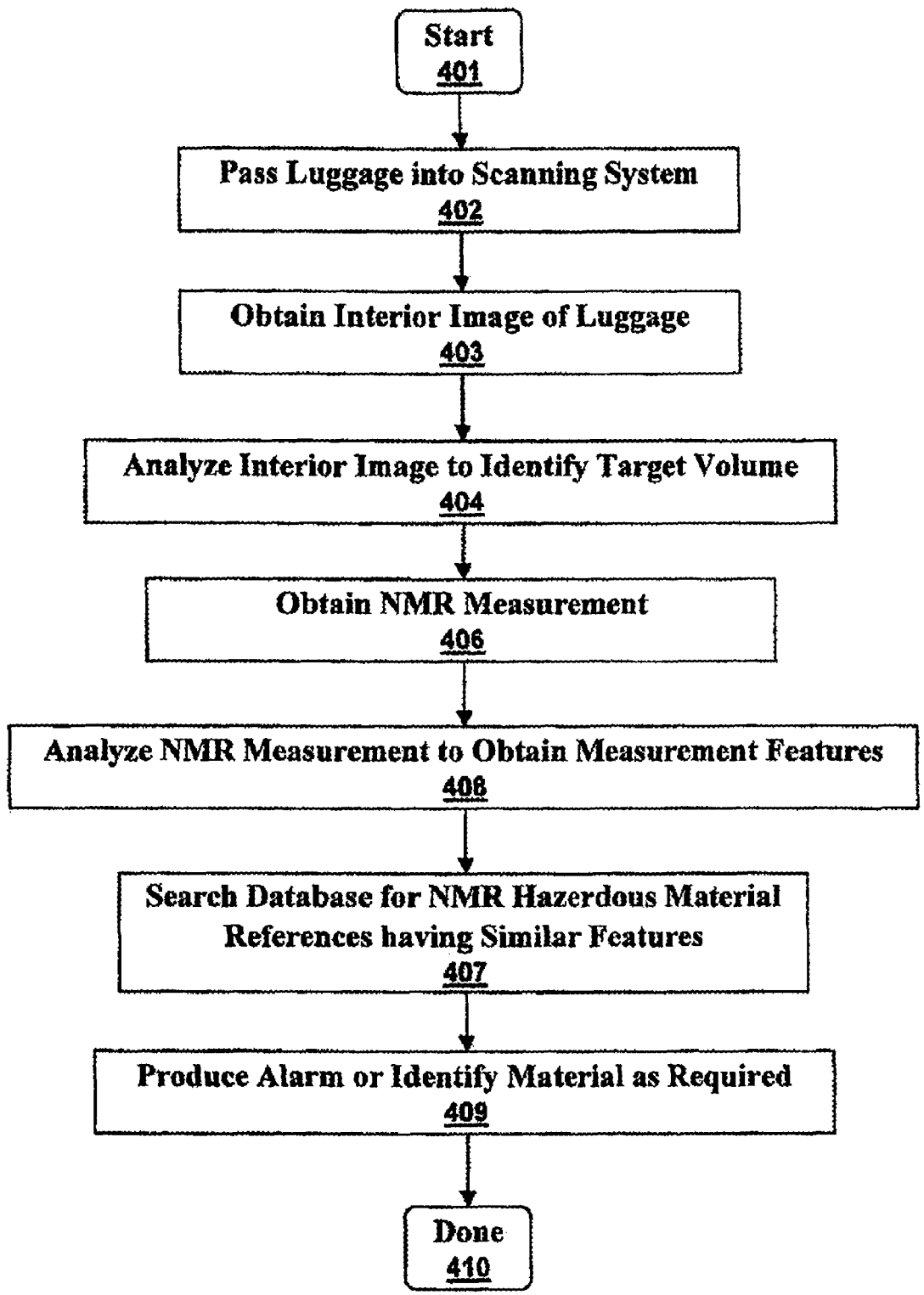
FIG. 4 illustrates a high level flow diagram of a method for locating target volumes and identifying materials of interest in accordance with aspects of some embodiments.

FIG. 4 illustrates a high level flow diagram of locating target volumes and identifying materials of interest in accordance with aspects of some embodiments. After the start 401, a container such as luggage is passed into the scanning system 402 and an interior image of the container is produced 403. The interior image can be analyzed to identify a target volume 404. An NMR measurement can be obtained 406 and analyzed to produce NMR measurement features 408. A database can then be searched for references similar to the NMR measurement features 407 and an alarm produced and the material identified if a matching reference is found in the database 409. Finally the process is done 410.

Embodiments can be implemented in the context of modules. In the computer programming arts, a module (e.g., a software module) can be implemented as a collection of routines, data structures, firmware and hardware that perform particular tasks or implement a particular algorithm, function, capability, or abstract data type.

The particular values and configurations discussed in these non-limiting examples can be varied and are cited merely to illustrate embodiments and are not intended to limit the scope of the invention. The phrases "an embodiment", "some embodiments", or "certain embodiments" do not necessarily refer to the same embodiment or any specific embodiment. It will be appreciated that various aspects of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

In all embodiments of the present invention, all ranges are inclusive and combinable. All numerical amounts are understood to be modified by the word "about" unless otherwise specifically indicated. All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

What is claimed is:

1. A method comprising:
   obtaining an NMR measurement from a sample wherein an ultra-low field NMR system probes the sample and produces the NMR measurement and wherein a sampling temperature, prepolarizing field, and measurement field are known;
   detecting the NMR measurement by means of inductive coils;
   analyzing the NMR measurement to obtain at least one measurement feature wherein the measurement feature comprises T1, T2, T1ρ, or the frequency dependence thereof; and,
   searching for the at least one measurement feature within a database comprising NMR reference data for at least one material to determine if the sample comprises a material of interest.

2. The method of claim 1 wherein the dependence of measurement features are obtained as a function of a Larmor frequency of from about 1 kHz to about 40 kHz.

3. The method of claim 1, wherein the dependence of measurement features are obtained as a function of the pre-polarizing field strength.

4. The method of claim 1 wherein the material of interest is a liquid hazardous material, a food, a beverage, a substance indicative of food quality, a pharmaceutical product, or a pharmaceutical by-product.

5. The method of claim 1 wherein the inductive coils form a sensor array.

6. The method of claim 1 wherein the sample is encased in a conductive shell.

7. The method of claim 1 wherein the sample is inside a mammalian body.

8. The method of claim 1, wherein the sample is a nonferromagnetic container.

9. A method comprising:
   measuring a sampling temperature;
   obtaining an NMR measurement and an interior image from a sample wherein an ultra-low field NMR system probes the sample and produces the NMR measurement and wherein a sampling temperature, prepolarizing field, and measurement field are known;
   detecting the NMR measurement by means of inductive coils;
   analyzing the NMR measurement to obtain at least one measurement feature;
   searching for the at least one measurement feature within a reference library comprising NMR reference data for at least one material to determine if the sample comprises a material of interest.

10. The method of claim 9 wherein the interior image is an NMR image produced by the ultra-low field NMR system.

11. The method of claim 9 wherein the magnetic coils form a sensor array, wherein spatial sensitivity encoding is used to provide an image of the target volume within the sample; and wherein the NMR measurement corresponds to a composition within the target volume.

12. The system of claim 9 further comprising identifying a target volume from the interior image, wherein the wherein the magnetic coils form a sensor array, wherein the spatial dependence of the prepolarizing and measurement fields are used to produce an image of the target volume, and wherein the NMR measurement corresponds to a composition with the target volume.

13. The method of claim 9 wherein the material of interest is a hazardous material, a food, a beverage, a substance indicative of food quality, a pharmaceutical product, or a pharmaceutical by-product.

14. A method comprising:
   passing an container through a scanning system comprising an ultra-low field NMR system wherein the container is unopened, wherein the ultra-low field NMR system probes the container and produces an NMR measurement and wherein a sampling temperature, prepolarizing field, and measurement field are known and wherein the pre-polarizing magnetic field and the measurement magnetic field are different;
   detecting the NMR measurement by means of inductive coils;
   analyzing the NMR measurement to obtain at least one measurement feature;
   searching for the at least one measurement feature within a database comprising comprising NMR reference data for at least one material to determine if the sample comprises a material of interest.

15. The method of claim 14 wherein the container is luggage.

16. The method of claim 14, wherein the container is a nonferromagnetic container.

17. The method of claim 14 wherein the container comprises a conductive shell.

18. The method of claim 14 wherein the container contains smaller containers comprising conductive shells.

19. The method of claim 14 further comprising obtaining an interior image of the container wherein the scanning system further comprises an interior imaging system.

20. The method of claim 19 further comprising identifying a target volume within the container, wherein the inductive coils form a sensor array, and wherein the NMR measurement corresponds to a composition with the target volume.

* * * * *